United States Patent [19]

McDonald

[11] 4,321,271
[45] Mar. 23, 1982

[54] HETEROCYCLIC AND ALIPHATIC GROWTH PROMOTORS

[75] Inventor: Brian G. McDonald, Mosspark, Scotland

[73] Assignee: Beecham Group Limited, England

[21] Appl. No.: 164,159

[22] Filed: Jun. 30, 1980

[30] Foreign Application Priority Data

Jul. 10, 1979 [GB] United Kingdom ............... 24025/79
Sep. 7, 1979 [GB] United Kingdom ............... 31147/79

[51] Int. Cl.$^3$ ................... A61K 31/445; A61K 31/40; A61K 31/13
[52] U.S. Cl. ..................... 424/267; 260/239 B; 260/326.5 R; 260/348.48; 424/244; 424/274; 424/325; 546/248; 564/1; 564/445; 564/462; 564/475; 564/476; 564/477; 564/503
[58] Field of Search ................ 546/248; 260/326.5 R, 260/239 B; 564/1, 462, 503, 445, 475, 476, 477; 424/267, 274, 244, 325

[56] References Cited

U.S. PATENT DOCUMENTS

2,143,388 1/1939 Schlack ........................ 546/248 X
3,868,384 2/1975 Szinai et al. ................. 546/248 X
3,898,237 8/1975 Grethe et al. ................. 546/248 X

OTHER PUBLICATIONS

Itoh, K., et al., *J. Org. Chem.*, 32, 2210–2213 (1967).
Reeve, W., et al., *J. Am. Chem. Soc.*, 86, 880–882 (1964).
Bowman, R., et al., *J. Chem. Soc.* (c), 1970, pp. 94–101.
Bishop, D., et al., *J. Chem. Soc.* (c), 1966, pp. 670–673.
Bishop, D., et al., *J. Chem. Soc.*, 1963, pp. 2381–2385.

*Primary Examiner*—Richard A. Schwartz
*Attorney, Agent, or Firm*—Jacobs & Jacobs

[57] ABSTRACT

Compounds of formula (I)

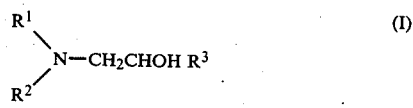

wherein:
$R^1$ is $C_{1-6}$ alkyl or $C_{5-7}$ cycloalkyl;
$R^2$ is hydrogen or $C_{1-6}$ alkyl; or
$NR^1R^2$ represents a heterocyclic ring having 5 to 7 ring atoms and only one hetero-atom; and
$R^3$ is $C_{1-4}$ alkyl, one carbon atom of which is di- or tri-halogenated or salts thereof are useful in promoting growth of ruminants. Processes for their production, veterinary formulations and treatments are described.

18 Claims, No Drawings

HETEROCYCLIC AND ALIPHATIC GROWTH PROMOTORS

This invention relates to compounds having the ability to promote growth in ruminant animals to compositions containing these compounds, and to a method for the preparation of these compounds.

U.S. Pat. No. 4,112,091 discloses a class of compounds of formula (A) below, precisely substituted piperazines:

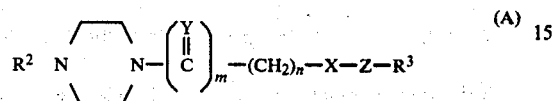

wherein $R^2$ is hydrogen, lower alkyl, lower hydroxyalkyl or phenyl optionally substituted with one lower alkyl or hydroxyalkyl group; Y is oxygen or sulphur; X is a group of formula a C=O, C=S or —CHOH; Z is oxygen, sulphur or a direct bond; $R^3$ is a straight—or branched-chain alkyl or alkenyl group, which is substituted at one methyl group by two or three halogen atoms, or is an adamantyl group; m is 0 or 1; and n is an integer from 0 to 4, provided that when m=0, then n=0; with the proviso that, when X is a group of formula —CHOH—, then m is 0, n is 1 and Z is a direct bond.

West German Offenlegungsschrift No. 2,553,021 discloses that a class of compounds of formula (B) below, precisely substituted 5-nitroimidazoles;

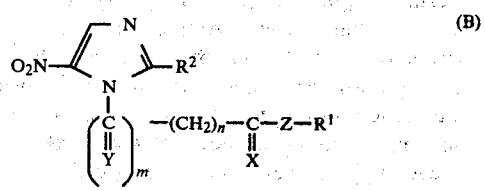

wherein $R^1$ is straight-chain or branched-chain alkyl or alkenyl optionally mono-substituted by phenyl or in which one methyl group is replaced by a mono-, di-, or trihalo-methyl group or $R^1$ is adamantyl or a phenyl optionally mono- or poly-substituted by $NO^2$, lower alkyl, lower alkozy, halogen or $CF_3$; $R^2$ is H or lower alkyl; X, Y and Z are the same or different O or S; n is 0, 1, 2, 3 or 4; and m is 0 or 1; provided that when m is 0, X and Z are both 0, n is 1-4 and $R^2$ is H or $CH_3$, then $R^1$ is other than benzyl, unsubstituted alkyl, or phenyl.

The compounds of formula (A) and (B) are stated to be useful feed additives for animals, especially ruminants, by virtue of their ability to inhibit methane formation and/or to displace fatty acid formation in favour of propionate formation.

It has now been discovered that a narrow class of compounds structurally distinct from the compounds of formulae (A) and (B) may be used as feed additives for ruminants to enhance their growth.

Accordingly, the present invention provides a compound of the formula (I):

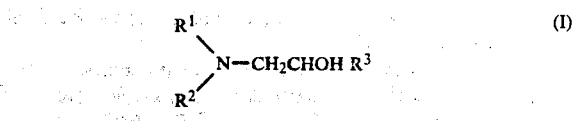

wherein:
$R^1$ is $C_{1-6}$ alkyl or $C_{5-7}$ cycloalkyl;
$R^2$ is hydrogen or $C_{1-6}$ alkyl; or
$R^1$ and $R^2$ together with the nitrogen atom to which they are joined represent a heterocyclic ring having 5 to 7 ring atoms and only the one hetero atom; and $R^3$ is $C_{1-4}$ alkyl, one carbon atom of which is di- or tri-halogenated;

or a salt thereof, for use as a growth promoter or as a veterinary composition together with a veterinarily acceptable carrier.

Suitable examples of $R^1$ include methyl, ethyl, n- and iso-propyl, n-, sec- and tert-butyl; and cyclohexyl.

Suitable examples of $R^2$ include hydrogen, methyl, ethyl, n- and iso-propyl, n-, sec, and tert-butyl.

Suitably $R^1$ and $R^2$, when $R^1$ is $C_{1-6}$ alkyl, contain no more than 5 carbon atoms.

As stated $R^1$ and $R^2$ together with the nitrogen atom to which they are joined can represent a ring. Suitably such $R^1R^2N-$ groups are pyrrolidino or piperidino.

Suitable examples of $R^3$ include chlorinated methyl and ethyl groups, such as tri-chloromethyl and 2,2,2-trichloroethyl.

One particularly useful sub-group of compounds within formula (I) are of formula (I)':

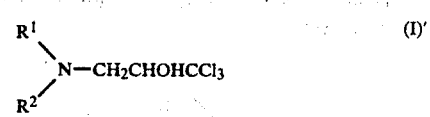

wherein:
$R^1$ is $C_{1-6}$ alkyl;
$R^2$ is hydrogen or $C_{1-6}$ alkyl.

Suitable values for $R^1$ and $R^2$ are as hereinbefore described for relevant $R^1$ and $R^2$ groups. Preferably $R^1$ and $R^2$ are both ethyl.

A second particularly useful sub-group of compounds within formula (I) are or formula (I)":

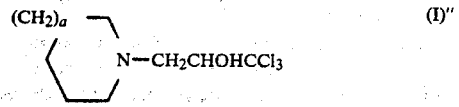

wherein:
a is 0, 1 or 2.

Preferably a is 0 or 1 in formula (I)", most preferably 1.

A third particularly useful sub-group of compounds within formula (I) are of formula (I)''':

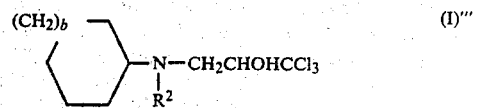

wherein:
b is 0, 1 or 2;
$R^2$ is as defined.

Suitably b is 1 in formula (I)'''.

Suitable examples of $R^2$ in formula (I)''' are as hereinbefore described.

Salts of compounds of the formula (I) include acid addition salts with acids such as hydrochloric acid.

In Itoh et al, *J. Org. Chem.*, 32, 2210, (1967) are disclosed compounds of formula (I) wherein
$R^3$ is trichloromethyl and $NR^1R^2$ is dimethylamine, diethylamine and piperidine, but no utility is disclosed for these compounds.

Accordingly, the present invention provides novel compounds of formula (I)

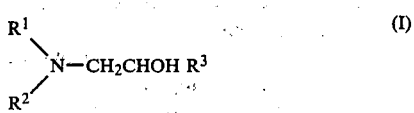

wherein:
$R^1$ is $C_{1-6}$ alkyl or $C_{5-7}$ cycloalkyl;
$R^2$ is hydrogen or $C_{1-6}$ alkyl; or
$NR^1R^2$ represents a heterocyclic ring having 5 to 7 ring atoms and only one hetero atom, and
$R^3$ is $C_{1-4}$ alkyl, one carbon atom of which is di- or tri halogenated;
and salts thereof,
provided that when $R^3$ is trichloromethyl, $NR^1R^2$ is other than dimethylamine, diethylamine and piperidine.

The invention also provides a process for the preparation of a compound of the formula (I), which process comprises reacting an amine of general formula $R^1R^2NH$ with a substituted propylene oxide of general formula (II):

The reaction may suitably be carried out by dissolving the reactants in an inert organic solvent, such as ethanol or ethyl acetate, and letting the reaction continue for an extended period of time at room temperature.

The salts of the compounds of the formula (I) can be prepared in the usual manner, for example by reacting a free base compound of the formula (I) with an acid.

Preferably the salt formed will be pharmaceutically acceptable.

The compositions containing compounds of the formula (I) are useful food additives for ruminants as they act as growth promoters by virtue of reduced or inhibited methane production and enhanced proportionate production.

The carrier may obviously be a food stuff in which case conveniently the composition can be formed in situ by addition of the compound of the formula (I) to the animal feed.

Alternatively, the composition containing the compound of the formula (I) may be administered to the animal separately from the feed, in which case the said veterinary composition will be a tablet, capsule, bolus, aqueous solution (which may be added to the drinking water) and the like. Such compositions may be formulated in conventional manner. Slow release formulations may also be used.

Clearly the active dose of the compound of the formula (I) will vary from compound to compound, and with the weight and nature of the ruminant concerned.

However, by way of illustration, it is believed that a level of compound in the diet of 1 to 1000 ppm, more suitably 1 to 200 ppm, will enable the beneficial effects of the compound to be obtained.

The following examples illustrate the preparation of compounds of the formula (I) and their activity in an in vitro test system.

EXAMPLE 1

1,1,1-Trichloro-3-methylaminopropan-2-ol

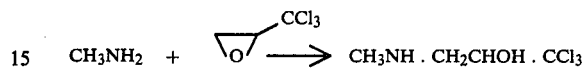

Trichloropropylene epoxide (2.2 ml) and methylamine (5 ml; 30% solution in water) were stirred together in ethanol (30 ml) at room temperature for 48 hours. On evaporation of the ethanol on a rotary evaporator, the product separated out as a white crystalline solid. The material was re-crystallized from ethyl acetate yielding white needles, 1.80 g; melting point 112°–114° C.

$C_4H_8NOCl_3$ requires: C, 24.94; H, 4.14; N, 7.27; Cl, 55.32, found: C, 25.20; H, 4.15; N, 7.12; Cl, 55.67.

EXAMPLE 2

1,1,1-Trichloro-3-dimethylaminopropan-2-ol

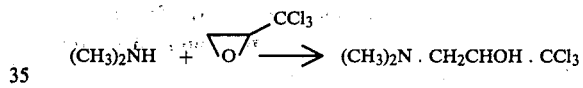

Trichloropropylene epoxide (3.2 g) and dimethylamine (5 ml of a 33% w/w solution in methylated spirits) were stirred together in ethanol (30 ml). The reaction became exothermic a few minutes after mixing and external ice-cooling was applied. After overnight stirring, the solution was concentrated on a rotary evaporator causing precipitation of the product (3.3 g). Re-crystallization from ethyl acetate yielded white needles, m.pt 119°–120° C.

$C_5H_{10}NOCl_3$ requires: C, 29.06; H, 4.84; N, 6.78; Cl, 51.57, found: C, 29.17; H, 4.63; N, 6.78; Cl, 51.63.

EXAMPLE 3

1,1,1-Trichloro-3-diethylaminopropan-2-ol

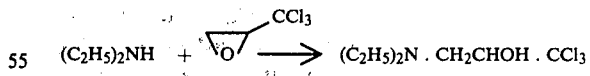

Diethylammonium chloride (3.0 g) was dissolved in dilute (2 N) sodium hydroxide solution and extracted with ethyl acetate (100 ml). To the stirring ethyl acetate solution was then added trichloropropylene epoxide (2.2 ml) and the reaction mixture stirred at room temperature for 3 days. The solvent was removed on a rotary evaporator to reveal the white solid product. This was crystallized from ethyl acetate.

Yield 1.85 g; m.pt 68°–70° C.

$C_7H_{14}NOCl_3$ requires: C, 35.82; H, 5.97; N, 5.97; Cl, 45.42, found: C, 35.96; H, 5.90; N, 5.99; Cl, 45.44.

EXAMPLE 4

1,1,1-Trichloro-3-isobutylaminopropan-2-ol

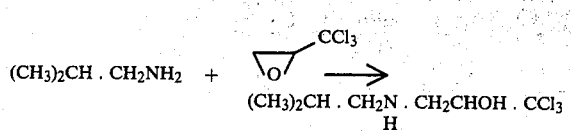

$(CH_3)_2CH \cdot CH_2NH_2 + \text{epoxide} \rightarrow (CH_3)_2CH \cdot CH_2N(H) \cdot CH_2CHOH \cdot CCl_3$ Isobutylamine (2 ml) and trichloropropylene epoxide (2.2 ml) were stirred together in ethyl acetate at room temperature for 20 hours. On reduction of the volume of the ethyl acetate, the product precipitated as white needles, m.pt 89°–91° C., yield 3.55 g. Re-crystallization was from ethyl acetate.

$C_7H_{14}NOCl_3$ requires: C, 35.82; H, 5.97; N, 5.97; Cl, 45.42; found: C, 35.98; H, 5.72; N, 5.98; Cl, 45.51.

EXAMPLE 5

1,1,1-Trichloro-3-cyclohexylaminopropan-2-ol

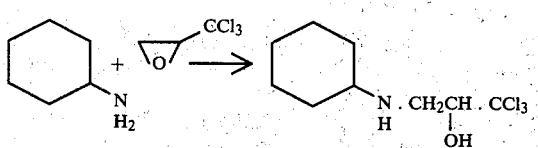

3,3,3-Trichloropropylene epoxide (3.2 g) in analar ethyl acetate (15 ml) was added dropwise, over a few minutes, to a solution of cyclohexylamine (2.0 g) in ethyl acetate (30 ml). The reaction mixture was then stirred at room temperature for 24 hours. Filtration gave a white solid (1.68 g). Concentration of the ethyl acetate solution gave a second crop of material, (1.76 g). Crystallization from ethyl acetate gave the product as white needles (m.pt 120°–121.5° C.).

$C_9H_{15}NOCl_3$ requires: C, 41.62; H, 5.78; N, 5.39; Cl, 41.04, found: C, 41.76; H, 6.19; N, 5.41; Cl, 41.56.

EXAMPLE 6

1,1,1-Trichloro-3-(N-piperidino)propan-2-ol

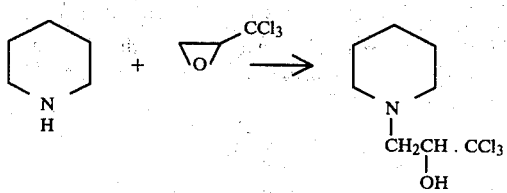

Piperidine (1.7 g) was mixed in ethyl acetate (20 ml), and added to a solution of 3,3,3-trichloropropylene epoxide (3.2 g) in ethyl acetate (40 ml). The solution was stirred at room temperature. After about 0.5 hours, it was observed that the solution was beginning to turn cloudy. After stirring at room temperature for 40 hours, the ethyl acetate was stripped off on a rotary evaporator, leaving the white solid product. This was taken up into solution in ethanol, and then precipitated by addition of water. This procedure was repeated. The product was filtered off, and dried under vacuum to leave a white amorphous powder, m.pt 96°–98° C.

$C_8H_{14}NOCl_3$ requires: C, 38.95; H, 5.68; N, 5.68; Cl, 43.20, found: C, 39.28; H, 6.0; N, 5.71; Cl, 44.21.

EXAMPLE 7

1,1,1-Trichloro-3-(N-pyrrolidino)propan-2-ol

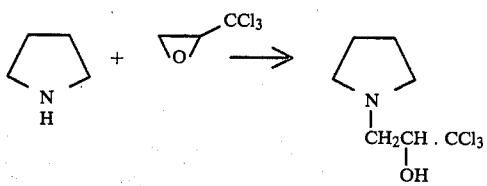

Pyrrolidine (1.4 g) and 3,3,3-trichloropropylene epoxide (3.2 g) were mixed together at room temperature in ethyl acetate (50 ml). After 18 hours, a white precipitate had formed. A white solid was filtered off, and washed with a little petrol. The material was vacuum dried (yield 2.32 g). The ethyl acetate solution was concentrated on a rotary evaporator and a further precipitate (1.72 g) filtered off. The material was re-crystallized from ethyl acetate, separating as white needles, m.pt 122°–123° C.

$C_7H_{12}NOCl_3$ requires: C, 36.13; H, 5.16; N, 6.02; Cl, 45.81, found: C, 36.32; H, 5.34; N, 5.99; Cl, 46.35.

In vitro Test Data Section

The compounds were tested for their ability to reduce or inhibit methane production and to enhance propionate formation. The method used is as follows:

The screening system is in vitro incubation of buffered rumen fluid with, or without, the addition of the test compound.

Rumen fluid is removed by suction from two rumen-fistulated sheep, just before feeding. The fluid is strained and mixed. The incubation is for twenty hours in a shaking water-bath at 39° C. Each incubation flask contains: 30 ml McDougall's bicarbonate buffer-pH 6.7–6.9, 10 ml strained rumen fluid, 200 mg substrate (the substrate is a ground sample of the diet on which the sheep has been fed) and 1 ml 10% aqueous ethanol containing 0.2% Tween 80 and the compound under examination. Samples are taken at the end of the incubation period for analysis of headspace gases and volatile fatty acids, by g.l.c.

The compounds were tested at 10 ppm/flask.

The results obtained are shown in the Table.

TABLE

| Compound of Example | Molar % VFA | | | μM/ml TVFA | VFA production % difference from control | | | | % inhibition of methane | % hydrogen present |
|---|---|---|---|---|---|---|---|---|---|---|
| | Acetate | Propionate | Butyrate | | Acetate | Propionate | Butyrate | TVFA | | |
| Control | 64.2 | 21.1 | 12.0 | 50.3 | — | — | — | — | — | 0.06 |
| 1 | 55.3 | 30.4 | 12.1 | 40.6 | −44.7 | +22.3 | −29.7 | −28.2 | 100 | 1.43 |
| 2 | 55.6 | 29.7 | 12.2 | 43.9 | −35.5 | +31.5 | −18.1 | −18.4 | 100 | 1.61 |
| 3 | 54.2 | 30.0 | 12.4 | 43.3 | −42.3 | +26.8 | −20.0 | −23.0 | 100 | 1.27 |
| 4 | 55.3 | 30.0 | 12.3 | 40.1 | −45.7 | +18.8 | −29.0 | −29.4 | 100 | 1.07 |
| Control | 65.3 | 23.7 | 8.77 | 47.8 | — | — | — | — | — | 0.002 |
| 5 | 56.7 | 31.1 | 10.21 | 44.2 | −31.1 | +32.5 | +14.6 | −11.8 | 100 | 1.01 |
| 6 | 57.7 | 30.7 | 9.64 | 45.3 | −25.8 | +34.1 | +7.9 | −8.3 | 100 | 1.34 |
| 7 | 57.7 | 30.5 | 9.67 | 44.6 | −27.6 | +30.5 | +5.6 | −10.4 | 100 | 1.18 |

TABLE-continued

| Compound of Example | Molar % VFA | | | μM/ml | VFA production % difference from control | | | | % inhibition of methane | % hydrogen present |
| --- | --- | --- | --- | --- | --- | --- | --- | --- | --- | --- |
| | Acetate | Propionate | Butyrate | TVFA | Acetate | Propionate | Butyrate | TVFA | | |
| A | 65.3 | 21.9 | 9.13 | 56.7 | −35.0 | +19.9 | +9.0 | −22.6 | 50.6 | 0.062 |
| 6* | — | — | — | — | −19.1 | +23.0 | +27.7 | −7.1 | 32.2 | 0.09 |

*Tested at 5 ppm level

These results show the ability of the compounds of the invention to reduce methane formation and to enhance propionate formation.

Compound A in the Table is the compound of formula:

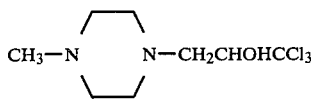

which is the compound of Example 11 of U.S. Pat. No. 4,112,091, and which is stated in the U.S. Patent at column 3, lines 55 to 58 to be one of the two 'most preferred compounds'. It is interesting to note that in the initial tests reported in the Table the compounds of the Examples are approximately twice as active methane inhibitors as this compound A.

In vivo Test Data Section

In vivo Studies in a "gas collection screen":

A Group of 4, 50 kg Sheep were fed diets containing the compound of Example 6 over 5 week period. A different sheep from each group was put into a respirometer for 24 hours each day. Each sheep was thus monitored once in every 5 days. Gas flow was maintained by a peristatic pump and measured using a commercial gas meter and a sub-sample collected in a butyl-rubber inner tube. Gas analysis was carried out by gas chromatograph using a R/E 204 gas chromatograph with both electron capture and home ionisation detectors.

During a run-in control period it was found the sheep produced 19.2±0.4 liters methane/day and not more than 1.5 liters Hydrogen/day.

The compounds were stable in the feed over the period of the study. By feeding measured amounts to the sheep (no refusals) it was possible to "dose" each sheep with 75 mg/day.

The results for the 5 week period are given in Table 2 below:

TABLE 2

| % inhibition of methanogenesis | Hydrogen evolution liters/24h |
| --- | --- |
| 9.1 | 2.1 |

I claim:

1. A veterinary composition for promoting the growth of ruminants, comprising a growth-promoting effective amount of a compound of formula (I):

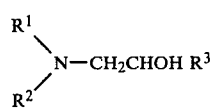

wherein:

$R^1$ is $C_{1-6}$ alkyl or $C_{5-7}$ cycloalkyl;
$R^2$ is hydrogen or $C_{1-6}$ alkyl; or
$NR^1R^2$ represents a saturated heterocyclic ring having 5 to 7 ring atoms and only one hetero-atom; and
$R^3$ is $C_{1-4}$ alkyl, one carbon atom of which is di- or tri-halogenated with the same halogen atom; or a pharmaceutically acceptable salt thereof;

in combination with a food stuff for the ruminant, said compound being present in said food stuff in an amount of from 1 to 1000 ppm.

2. The composition according to claim 1, wherein $R^3$ is trichloromethyl and $NR^1R^2$ is dimethylamino or piperidino.

3. The composition according to claim 1, wherein said compound is 1,1,1-trichloro-3-methylaminopropan-2-ol.

4. The composition according to claim 1, wherein said compound is 1,1,1-trichloro-3-dimethylaminopropan-2-ol.

5. The composition according to claim 1, wherein said compound is 1,1,1-trichloro-3-diethylaminopropan-2-ol.

6. The composition according to claim 1, wherein said compound is 1,1,1-trichloro-3-isobutylaminopropan-2-ol.

7. The composition according to claim 1, wherein said compound is 1,1,1-trichloro-3-cyclohexylaminopropan-2-ol.

8. The composition according to claim 1, wherein said compound is 1,1,1-trichloro-3-(N-piperidino)propan-2-ol.

9. The composition according to claim 1, wherein said compound is 1,1,1-trichloro-3-(N-pyrrolidino)propan-2-ol.

10. A method for promoting the growth of ruminants, which comprises administering to the ruminant a growth-promoting effective amount of a compound of formula (I)

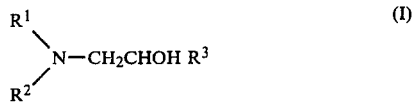

wherein:

$R^1$ is $C_{1-6}$ alkyl or $C_{5-7}$ cycloalkyl;
$R^2$ is hydrogen or $C_{1-6}$ alkyl; or
$NR^1R^2$ represents a saturated heterocyclic ring having 5 to 7 ring atoms and only one hetero-atom; and
$R^3$ is $C_{1-4}$ alkyl, one carbon atom of which is di- or tri-halogenated with the same halogen atom; or a pharmaceutically acceptable salt thereof.

11. The method according to claim 10, wherein $R^3$ is trichloromethyl and $NR^1R^2$ is dimethylamino or piperidino.

12. The method according to claim 10, wherein said compound is 1,1,1-trichloro-3-methylaminopropan-2-ol.

13. The method according to claim 10, wherein said compound is 1,1,1-trichloro-3-dimethylaminopropan-2-ol.

14. The method according to claim 10, wherein said compound is 1,1,1-trichloro-3-diethylaminopropan-2-ol.

15. The method according to claim 10, wherein said compound is 1,1,1-trichloro-3-isobutylaminopropan-2-ol.

16. The method according to claim 10, wherein said compound is 1,1,1-trichloro-3-cyclohexylaminopropan-2-ol.

17. The method according to claim 10, wherein said compound is 1,1,1-trichloro-3-(N-piperidino)propan-2-ol.

18. The method according to claim 10, wherein said compound is 1,1,1-trichloro-3-(N-pyrrolidino)propan-2-ol.

* * * * *